(12) United States Patent
Bindayel (10) Patent No.: US 9,795,456 B2
(45) Date of Patent: *Oct. 24, 2017

(54) ORTHODONTIC SYSTEMS

(71) Applicant: Naif Bindayel, Riyadh (SA)

(72) Inventor: Naif Bindayel, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 15/160,275

(22) Filed: May 20, 2016

(65) Prior Publication Data

US 2017/0128165 A1 May 11, 2017

Related U.S. Application Data

(60) Provisional application No. 62/252,760, filed on Nov. 9, 2015.

(51) Int. Cl.
| | | |
|---|---|---|
| A61C 3/00 | (2006.01) |
| A61B 90/98 | (2016.01) |
| A61C 7/00 | (2006.01) |
| A61C 7/12 | (2006.01) |
| A61C 7/14 | (2006.01) |
| A61C 7/22 | (2006.01) |
| A61C 7/28 | (2006.01) |
| A61B 90/00 | (2016.01) |

(52) U.S. Cl.
CPC ............. *A61B 90/98* (2016.02); *A61C 7/002* (2013.01); *A61C 7/12* (2013.01); *A61C 7/14* (2013.01); *A61C 7/22* (2013.01); *A61C 7/28* (2013.01); *A61B 2090/064* (2016.02); *A61B 2560/0219* (2013.01); *A61B 2560/045* (2013.01)

(58) Field of Classification Search
CPC .. A61C 7/12; A61C 7/14; A61C 7/141; A61C 7/143; A61C 7/285; A61C 7/145; A61C 7/148; A61C 7/17; A61C 7/18; A61C 7/28; A61C 7/22; A61C 7/297; A61C 7/30; A61C 7/34; A61C 1/003; A61C 1/04; A61C 1/06; A61B 90/98; A61B 2090/064; A61B 2560/0219; A61B 2560/045; A61B 2560/045
USPC ....................................... 433/8–18
See application file for complete search history.

(56) References Cited

U.S. PATENT DOCUMENTS

| | | | |
|---|---|---|---|
| 4,292,025 A * | 9/1981 | Forster ................ | A61C 7/00 433/18 |
| 5,032,080 A | 7/1991 | Hakansson et al. | |
| 5,954,502 A * | 9/1999 | Tuenge ................ | A61C 7/14 433/16 |

(Continued)

OTHER PUBLICATIONS

International Search Report and Written Opinion of the International Searching Authority for International Application No. PCT/IB2016/056759 dated Apr. 4, 2017.

(Continued)

*Primary Examiner* — Heidi M Eide
(74) *Attorney, Agent, or Firm* — Fish & Richardson P.C.

(57) ABSTRACT

An orthodontic system includes an orthodontic bracket that defines an arch wire slot. The bracket includes a gear system, a motor to drive the gear system, and an integrated circuit to control the motor, an arch wire placed in the arch wire slot, and a computer server to send instructions to the integrated circuit in the orthodontic bracket. The integrated circuit is configured to control the motor according to the instructions from the computer server to drive the gear system to apply a force to the arch wire.

43 Claims, 7 Drawing Sheets

(56) References Cited

U.S. PATENT DOCUMENTS

| | | | |
|---|---|---|---|
| 6,632,088 B2 * | 10/2003 | Voudouris | A61C 7/12 433/18 |
| 7,306,458 B1 | 12/2007 | Lu | |
| 7,581,714 B2 | 9/2009 | Machu | |
| 9,531,237 B2 | 12/2016 | Miller | |
| 2001/0029008 A1 | 10/2001 | Jordan et al. | |
| 2003/0031975 A1 | 2/2003 | Voudouris | |
| 2003/0152889 A1 | 8/2003 | Uji | |
| 2005/0269821 A1 | 12/2005 | Nadel et al. | |
| 2006/0074431 A1 | 4/2006 | Sutton et al. | |
| 2007/0184399 A1 | 8/2007 | Salich | |
| 2008/0248439 A1 | 10/2008 | Griffith et al. | |
| 2009/0286195 A1 | 11/2009 | Sears et al. | |
| 2009/0317757 A1 | 12/2009 | Lemchen | |
| 2012/0148973 A1 | 6/2012 | Johnston | |
| 2014/0134562 A1 | 5/2014 | Wu et al. | |
| 2015/0305833 A1 | 10/2015 | Cosse | |

OTHER PUBLICATIONS

Non-Final Office Action for U.S. Appl. No. 15/160,234 dated Apr. 10, 2017.
Non-Final Office Action for U.S. Appl. No. 15/160,255 dated Apr. 5, 2017.
Non-Final Office Action for U.S. Appl. No. 15/160,291 dated Apr. 7, 2017.

* cited by examiner

ORTHODONTIC SYSTEMS

CROSS-REFERENCE TO RELATED APPLICATIONS

This application claims priority to U.S. Provisional Patent Application 62/252,760, filed on Nov. 9, 2015. This application is related to U.S. patent application Ser. No. 15/160,234, filed on May 20, 2016, Ser. No. 15/160,291, filed on May 20, 2016, Ser. No. 15/160,277, filed on May 20, 2016, Ser. No. 15/160,255, filed on May 20, 2016, and Ser. No. 15/160,337, filed on May 20, 2016. The contents of the above applications are incorporated by reference in their entirety.

TECHNICAL FIELD

This disclosure relates to orthodontic systems.

BACKGROUND

Orthodontic braces are useful in correcting alignment of teeth to proper positions and orientations in the dental arch and to improve dental health. In some examples, orthodontic braces include metal brackets bonded to the teeth and arch wires that are tied to the brackets by elastic ties. The arch wires are designed to apply force to the brackets and teeth, causing the teeth to slowly move or rotate in prescribed directions. The arch wires are adjusted, e.g., every three or four weeks during treatment to maintain pressure in order to supply prescribed forces to the teeth. There are many types of dental braces. For example, braces can be self-ligating such that the arch wire clips into the brackets without the need for ligatures. Some dental braces use computer-adjusted wires. These braces use the same principle of force delivery by an external source outside of the bracket (e.g., wire, coils, or elastics). In some examples, a bracket may have a base that is angulated to combine torque, angulation, in and out bend, and offsets for each tooth. This enables an unadjusted arch wire to perform variant alignment functions (i.e., with no further wire bending). In some examples, a series of clear molds may be used to produce teeth alignment. Orthodontic treatments generally last for two to three years.

SUMMARY

In a general aspect, an orthodontic bracket includes a base configured to be attached to a surface of a tooth, and a first member and a second member both attached to the base, in which the first and second members are spaced apart to define an archwire slot configured to receive an archwire. The first member includes a first gear and a first rod, the first rod has a first portion having notches that engage the gear, the first rod has a second portion that extends into the archwire slot, and when the first gear rotates in a specified direction, the first gear drives the first rod to contact the archwire and apply a first force to the archwire.

In another general aspect, a method for orthodontic treatment includes attaching a base of an orthodontic bracket to a surface of a tooth, the orthodontic bracket having a base, a first member and a second member, the first member and the second member being attached to the base and spaced apart to define an archwire slot, in which the first member includes a first gear and a first rod, the first rod has a first portion having notches that engage the first gear, and the first rod has a second portion that extends into the archwire slot. The method includes inserting an archwire into the archwire slot; and rotating the first gear to drive the first rod to contact the archwire and apply a first force to the archwire.

In another general aspect, an orthodontic bracket includes a base configured to be attached to a surface of a tooth; and an occlusal member and a gingival member both attached to the base, the occlusal member and the gingival member being spaced apart to define an archwire slot between a gingival surface of the occlusal member and an occlusal surface of the gingival member, in which the archwire slot is configured to receive an archwire. The occlusal member includes a first miniature gear and a first miniature rod that function as a rack and pinion gear system, the first rod has an occlusal portion having notches that engage the gear, the first rod has a gingival portion that protrudes through the gingival surface of the occlusal member into the archwire slot, when the first gear rotates in a specified direction, the first gear drives the first rod to contact the archwire and apply a first force to the archwire.

Other aspects include other combinations of the features recited above and other features, expressed as methods, apparatus, systems, program products, and in other ways. Advantages of the aspects and implementations may include one or more of the following. The orthodontic brackets can be active brackets or smart brackets. A remote orthodontic system can allow active brackets or smart brackets to be remotely controlled or adjusted. The active brackets can generate force, and the force applied to the teeth can be increased or decreased while the patient is at home. The progress of teeth alignment can be monitored remotely. The remote orthodontic system can provide feedback and report symptoms, if any, to the orthodontist. In cases where adjustments to the original treatment plans are needed, the force adjustments can be made and applied while the patient is at home without the need to visit the dental clinic. The system can also provide an estimate of the remaining treatment time based on current progress of treatment. The system can reduce the trial and error in orthodontic treatment by using proper biomechanical pre-planning and insistent re-adjustment and monitoring. The system can improve the accessibility for orthodontic treatment in rural areas, and may reduce the number of days that school children miss classes. The orthodontic treatment outcomes may be more predictable, leading to a better quality with potentially reduced treatment side effects.

DESCRIPTION OF DRAWINGS

Like reference symbols in the various drawings indicate like elements.

DETAILED DESCRIPTION

This document describes an orthodontic system that enables an orthodontist to remotely monitor orthodontic braces on patients and make adjustments when necessary in a precise and predictable manner. In some implementations of the remote orthodontic system, the orthodontic system includes smart brackets in which each bracket has a miniature motor that drives a miniature gear, which in turn drives small rods or posts that push against an arch wire, generating a reaction force that pushes against the bracket's wings, in which the reaction force is transferred to the corresponding tooth to provide the required force for alignment of the tooth. The number of miniature motors and the configuration of the motor(s) can vary depending on design and functions. For example, the orthodontic system can include smart brackets in which each bracket has two miniature motors that drive miniature gears, which in turn pull or push an arch wire to generate opposing forces for alignment of the corresponding tooth (by generating couple forces system). In other implementations of the remote orthodontic system, the orthodontic system includes smart brackets in which each bracket has one or more miniature motors that drive one or more miniature gears, which in turn drive a rotatable base to provide root torque to the bracket for generating a force for alignment of the corresponding tooth. In some implementations of the remote orthodontic system, the orthodontic braces include arch wire segments connected by smart brackets in which each bracket has one or more miniature motors that apply forces to the arch wire segments, such that the combination of the forces generated by the plurality of brackets provide the proper amount of force for the alignment of each individual tooth.

Figure 1:
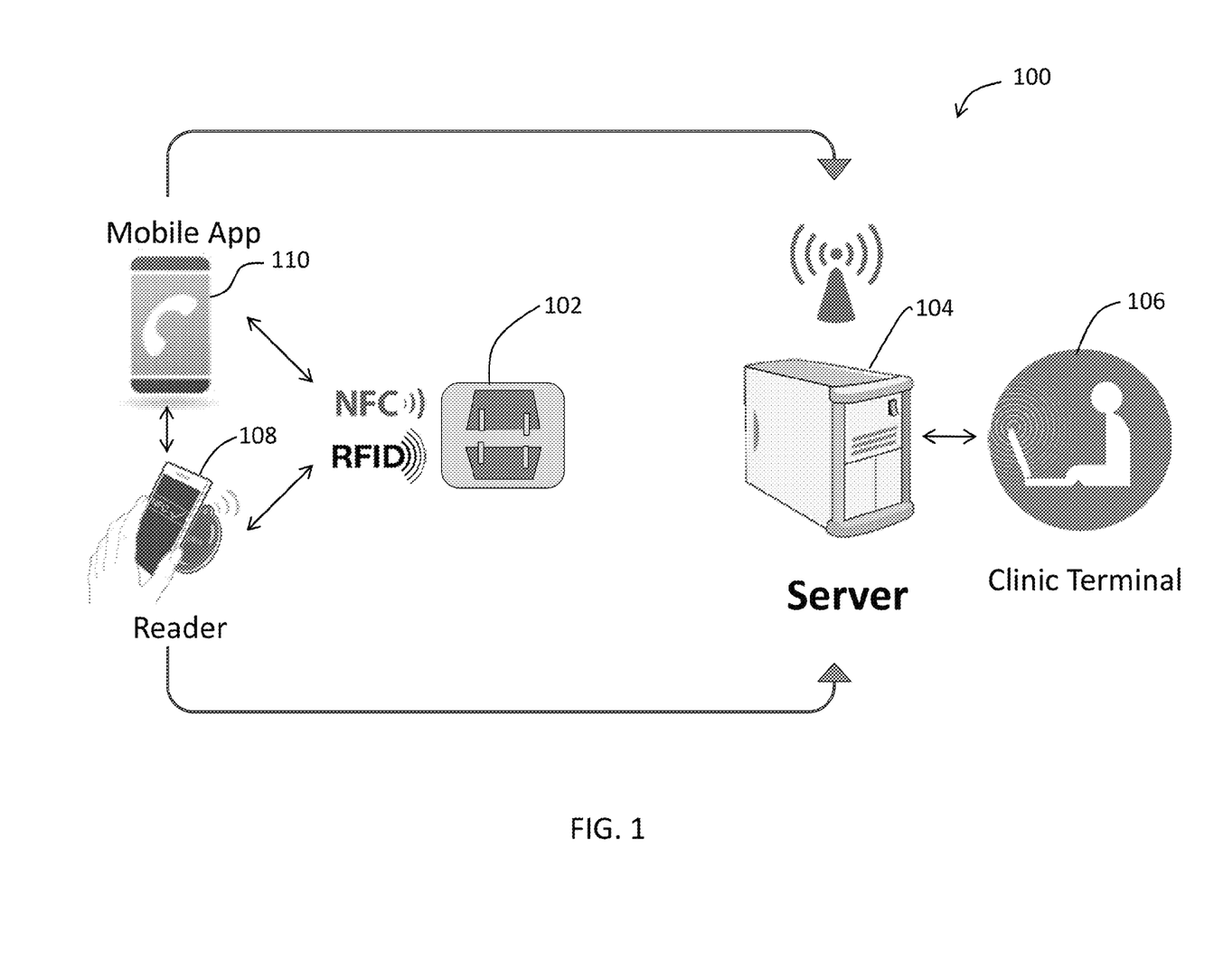
FIG. 1 is a diagram of an exemplary remote orthodontic system.

Referring to FIG. 1, a remote orthodontic system 100 includes orthodontic braces composed of smart brackets 102 (only one is shown in the figure) that communicate wirelessly with a computer server 104. The computer server 104 can be a physical machine located at the patient's home, or it can be a virtual server commonly referred to as a cloud server that resides remotely. The following describes examples in which the computer server 104 is a cloud server. In some examples, the computer server 104 may interact wirelessly with the brackets 102 by receiving signals from or sending signals to the brackets 102. This interaction occurs through, e.g., a home-based reader 108 or a user's cell phone 110, while the computer server 104 communicates with a clinic terminal 106 at a dental clinic. The computer server 104 receives signals from the brackets 102 (e.g., through the reader 108 or the cell phone 110), determines the current configurations of the brackets 102, determines whether adjustments are necessary, and sends back signals using the same route (e.g., through the reader 108 or the cell phone 110) to the brackets 102 in order to control motors in the brackets 102 to make the necessary adjustments. The computer server 104 communicates with the terminal 106 at the dental clinic to enable an orthodontist and/or other healthcare providers to monitor the configurations of the brackets 102 and enter commands to make additional adjustments when necessary.

In some implementations, when the patient first visits the orthodontist, the orthodontist may prescribe a treatment plan that specifies the amount and direction of force to be applied to each tooth at different time periods. The orthodontist may provide an electronic file that includes the treatment plan, and the patient may download, from the computer server 104, the electronic file having updated data containing the treatment plan to the reader 108 or the cell phone 110. The reader 108 or the cell phone 100 may execute an orthodontic application program that uses the information about the treatment plan to interact with the brackets 102.

After the first visit to the orthodontist, and at each follow up visit every three or four weeks, the orthodontist executes the orthodontic treatment program on the server 104. The orthodontic treatment program may analyze signals received from the brackets 102 to determine the progress of teeth alignment. The program may compare the current progress with the prescribed treatment plan and determine which brackets need to be adjusted to increase or decrease the force applied and its direction to the corresponding tooth, or to adjust the torque applied by the bracket to the tooth. The program instructs the server 104 to send signals to the brackets 102 to configure the brackets 102 such that each tooth receives the proper amount of force metrics according to the prescribed treatment plan.

Because the adjustments to the brackets 102 can be conveniently performed at the patient's home, the treatment plan may have instructions for more frequent bracket adjustments at finer time intervals, such as twice every month. The patient has the option of making adjustments to the brackets at times that are convenient to the patient.

The wireless reader 108 can interact wirelessly with the brackets 102 using a communication protocol similar to, e.g., the RFID protocol, Bluetooth protocol, or other protocols. The wireless reader 108 may be connected to the computer server 104 through a wire connection or a wireless link. The mobile phone 110 executing the orthodontic application program may interact wirelessly with the brackets 102 using a communication protocol similar to, e.g., the near-field communication protocol, Bluetooth protocol, or other protocols. The system may operate in, e.g., the 401-406 MHz, 902-928 MHz, 2400-2483.5 MHz, and/or 5725-5850 MHz bands. The mobile phone 110 may communicate with the computer server 104 through a wireless link.

In some implementations, the smart bracket 102 has sensors that can detect the amount of force (and/or the position trajectories) being applied to the tooth through the arch wire. Alternatively the sensors can be attached to or embedded in the arch wire itself. The sensors provide feedback signals so that the orthodontic treatment program executing on the computer server 104 can determine that the correct amount of force and the direction of force are applied to each tooth to ensure its proper alignment and positioning. If, after configuring the brackets 102, the sensors determine that the force/direction applied to the tooth deviates from the prescribed amount by more than a threshold value, the program may generate an alert signal, indicating that the patient should contact the orthodontist. Alternatively, the program can readjust and apply the new biomechanical force specifications. Upon receiving an instruction from the patient, the computer server 104 may send the data from the sensor to the clinic terminal 106 so that the orthodontist may determine whether it is possible to reconfigure the brackets remotely, or to inform the patient that it is necessary to return to the dental clinic for further examination and adjustment.

Figure 2:
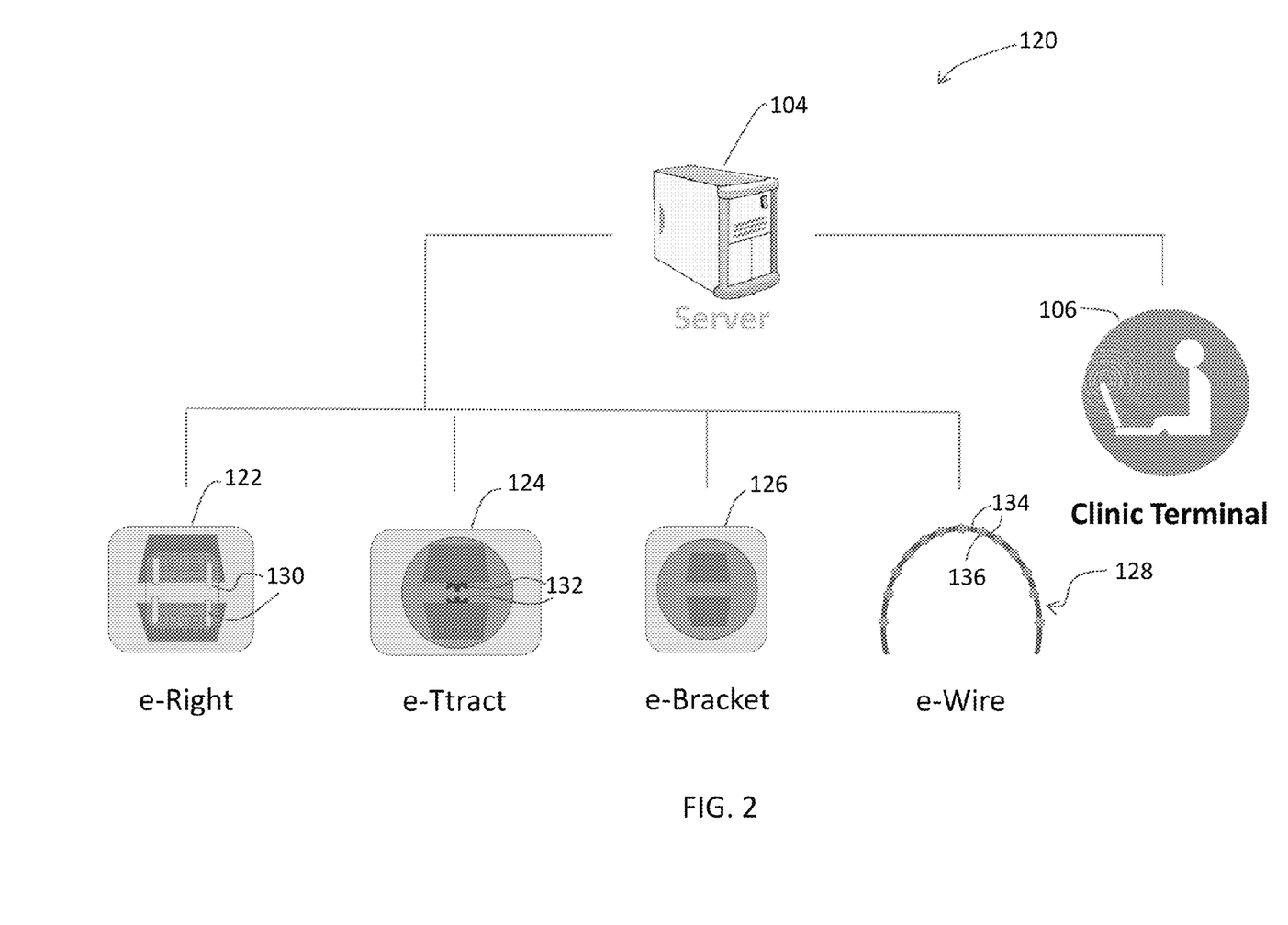
FIG. 2 is a diagram of various modules of the remote orthodontic system.

Referring to FIG. 2, a remote orthodontics system 120 may include a server 104 that communicates with different types of smart orthodontic braces, or orthodontic braces that include more than one type of smart brackets (individually or as a group). The computer server 104 may execute an orthodontic treatment program that is configured to control the various types of braces having various types of smart brackets. The server 104 may communicate with a clinic terminal 106 to enable an orthodontist to remotely monitor treatment progress or provide adjustments.

For example, one type of smart bracket is bracket 122, referred to as the e-Right bracket. The e-Right bracket 122 includes miniature motors that drive miniature gears, which in turn drive small rods 130 that push against an arch wire inserted into a slot of a bracket attached to a tooth. The small rods 130 provide forces that in combination produce the desired amount of force in the desired direction that is applied to the corresponding tooth to provide the required movement for alignment of the tooth.

A second type of smart bracket is bracket 124, referred to as the e-Tract bracket. The e-Tract bracket has two miniature motors that drive miniature gears 132, which in turn pull or push an arch wire (inserted in between) to generate retracting or protracting forces for movement and/or alignment of the corresponding tooth (or a group of teeth).

A third type of smart bracket is bracket 126, referred to as the e-Bracket in this document. The e-Bracket has one or more miniature motors that drive one or more miniature gears, which in turn drive a rotatable base to provide torque to the bracket 126 for generating a force for alignment of the corresponding tooth.

A fourth type of orthodontic braces variation is e-Wire braces 128. The e-Wire braces 128 include arch wire segments 134 connected to smart brackets 136 in which each bracket 136 has one or more miniature motors that apply forces to the arch wire segments 134, such that the interaction of the brackets 136 and wire segments 134 result in the proper amount of forces being applied to the teeth that need adjustment. Each arch wire segment is attached to the corresponding tooth surface in order to translate the delivered force. A patient may use any configuration of two or more of the e-Right bracket 122, e-Tract bracket 124, e-Bracket 126, or e-Wire braces 128 at the same time.

Figure 3:
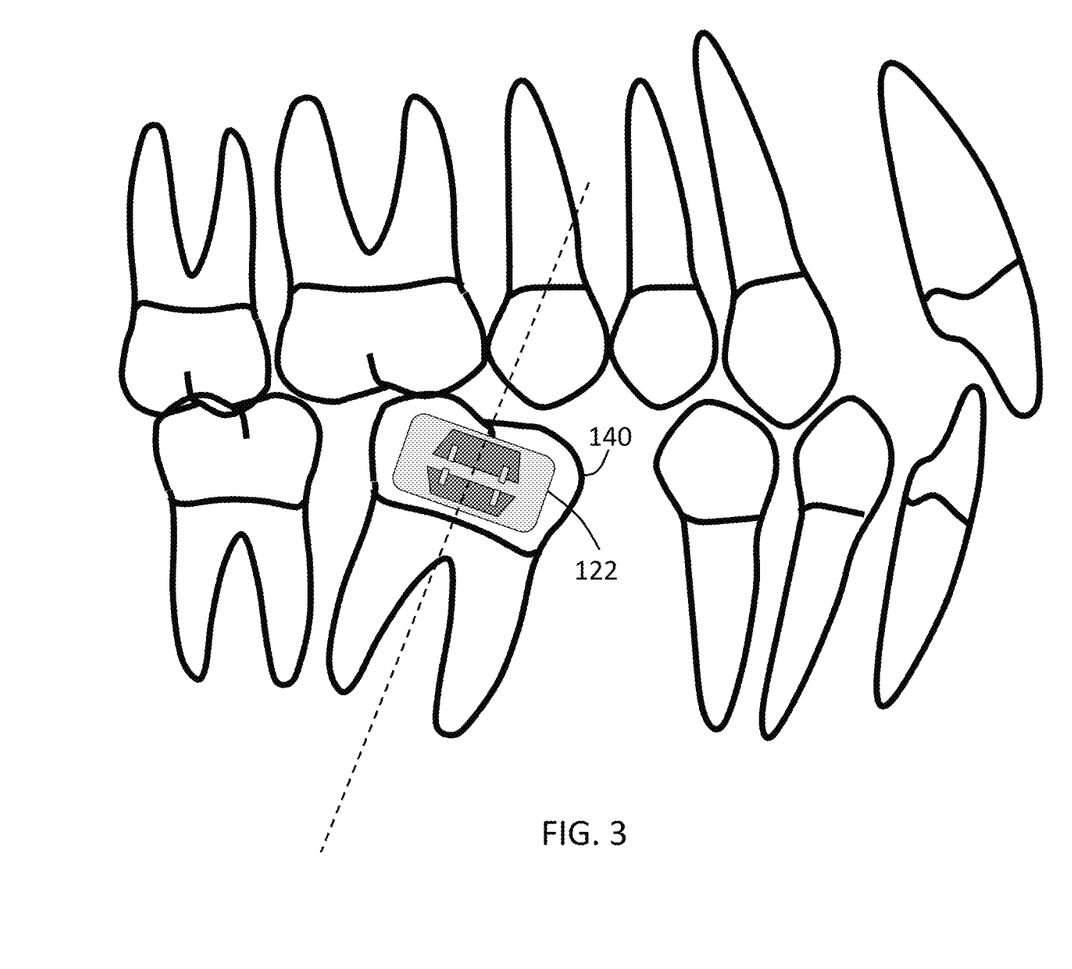
FIG. 3 is a diagram of an e-Right bracket.

Referring to FIG. 3, an e-Right bracket 122 may be attached to a tooth 140 (in this example, a molar tooth) and provide a force for moving the tooth. This is useful for up-righting a misaligned tooth (e.g., mesially tilted tooth).

Figure 4A:
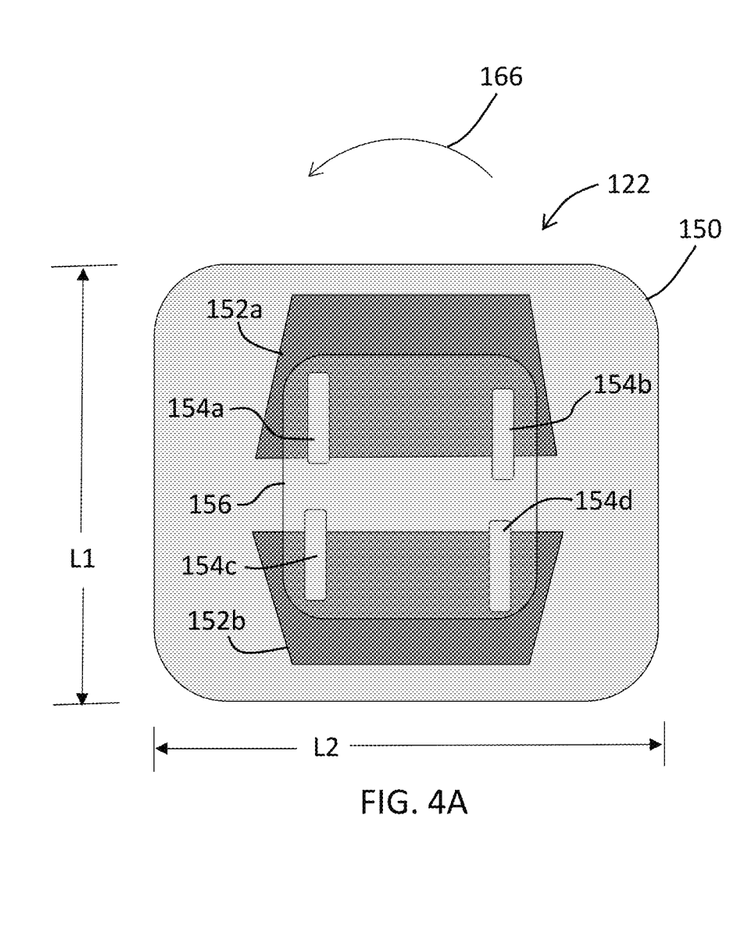
FIGS. 4A, 4B, 5A, and 5B are diagrams of an exemplary e-Right bracket.
Figure 4B:
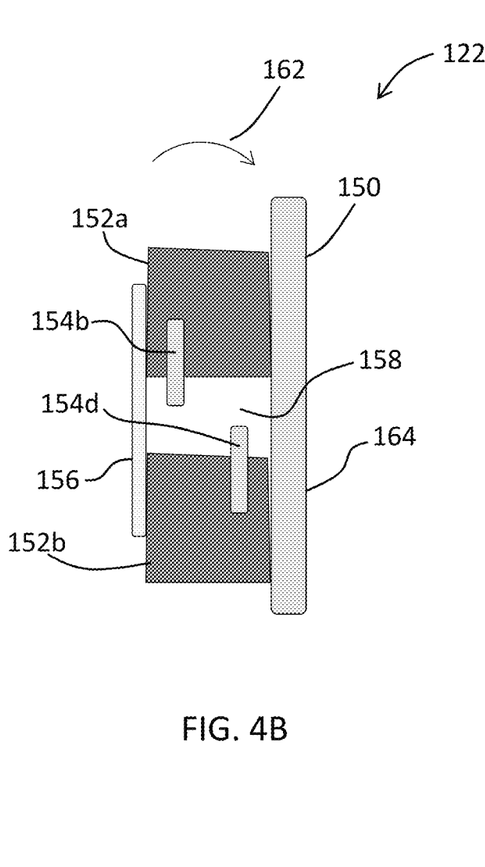

FIG. 4A is a front view of the e-Right bracket 122, and FIG. 4B is a side view of the e-Right bracket 122. The e-Right bracket 122 includes a base 150, an upper support 152a, a lower support 152b, and a cover 156. A serrated surface 164 of the base 150 attaches to a tooth that is subject to treatment. The upper support 152a and lower support 152b are connected to the base 150. The upper support 152a provides support for upper rods 154a and 154b that may protrude from the upper support 152a into a space 158 between the upper support 152a and the lower support 152b. The lower support 152b provides support for lower rods 154c and 154d that may protrude from the lower support 152b into the space 158. The cover 156 enables arch wire engagement within the space 158 so the operations of the rods 154a to 154d can have effect on the arch wire and eventually produce tooth movement.

An orthodontic arch wire 160 (see FIGS. 5A and 5B) passes through the space 158 between the upper rods 154a, 154b and the lower rods 154c, 154d. The orthodontic arch wire 160 conforms to the dental arch and passes through various brackets attached to the teeth whose alignment need adjustment or to serve as anchor points. The cover 156 can be either fixed or removable, and is used to ligate the arch wire 160 with the bracket slot. As the upper rods 154a, 154b and lower rods 154c, 154d push against the arch wire 160, the reaction forces (couple force system) pushing back against the rods generate a force and/or torque that is applied to the bracket 122. Since the bracket 122 is securely attached to the tooth, the force and/or torque is transferred to the tooth, providing the necessary forces for alignment of the tooth.

In some implementations, the rods 154a and 154b are driven by a first miniature gear in counter directions such that if the rod 154a is driven upwards, then the rod 154b is also driven downwards. Alternatively, if the rod 154a is driven downwards, then the rod 154b is driven upwards. Similarly, the rods 154c and 154d are driven by a second miniature gear in counter directions such that if the rod 154c is driven upwards, then the rod 154d is also driven downwards. Alternatively, if the rod 154c is driven downwards, then the rod 154d is driven upwards.

Figure 5A:
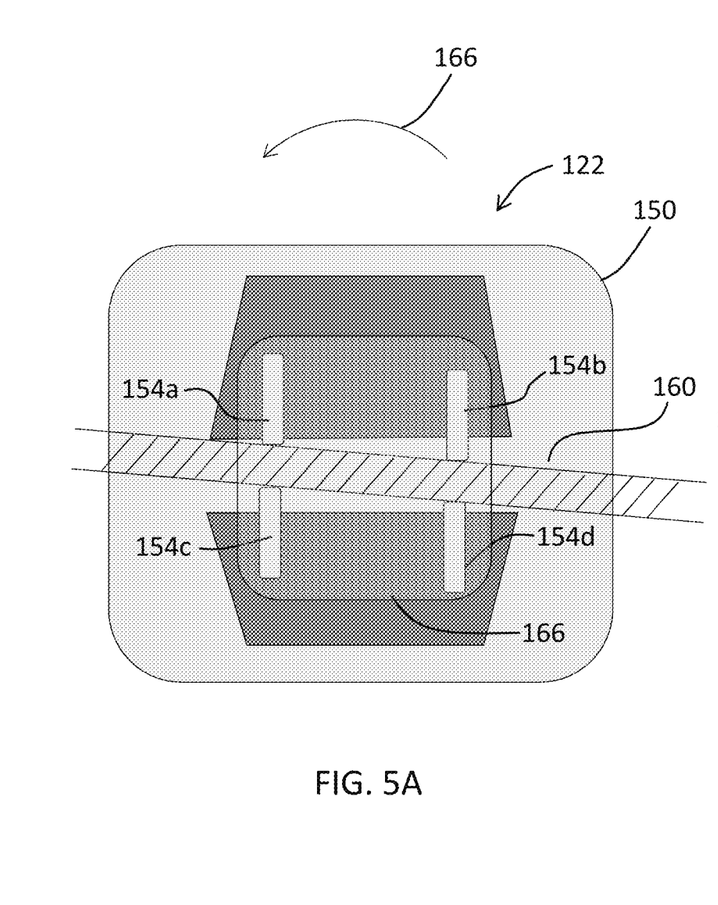

In the example shown in FIGS. 4A and 5A, the upper rod 154b is lower than the upper rod 154a, and the lower rod 154d is lower than the lower rod 154c. This causes the arch wire 160 to push against the upper rod 154b and the lower rod 154c, generating a counterclockwise rotation 166 on the bracket 122 about an axis perpendicular to the plane of the base 150 (when viewed from a direction facing the bracket 122).

Similarly, when the upper rod 154b is higher than the upper rod 154a, and the lower rod 154d is higher than the lower rod 154c, the arch wire 160 pushes against the upper rod 154b and the lower rod 154c, generating a clockwise torque 166 on the bracket 122 about an axis perpendicular to the plane of the base 150 (when viewed from a direction facing the bracket 122).

In some implementations, as shown in FIG. 4B, the upper rods 154a and 154b are substantially aligned along a first plane parallel to a surface of the base 150, i.e., the distance between the rod 154a to the base 150 is substantially the same as the distance between the rod 154b to the base 150. The lower rods 154c and 154d are substantially aligned along a second plane parallel to the surface of the base 150, i.e., the distance between the rod 154c to the base 150 is substantially the same as the distance between the rod 154d to the base 150. The first plane can be offset relative to the second plane, such that the distance between the upper rods 154a, 154b to the base 150 is different from the distance between the lower rods 154c, 154d to the base 150.

Figure 5B:
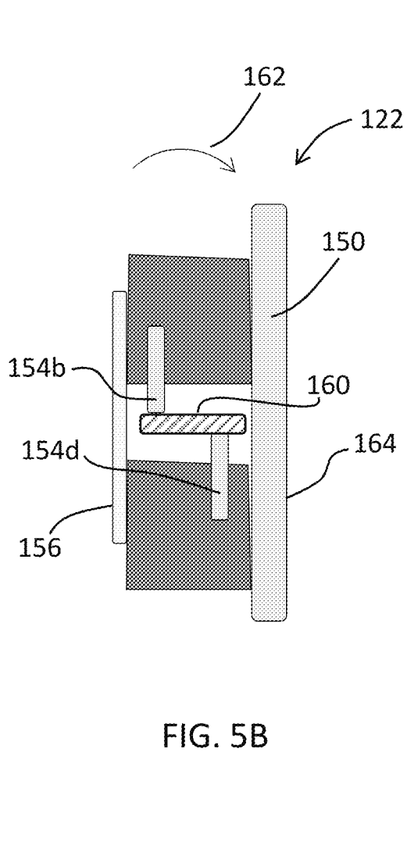

In the example shown in FIGS. 4B and 5B, the upper rod 154b is farther from the base 150 than the lower rod 154d. This causes the arch wire 160 to push against the upper rod 154b and the lower rod 154d, generating a clockwise rotational torque 162 on the bracket 122 about an axis parallel to the plane of the base 150 (when viewed along a direction facing a right side of the bracket 122). Similarly, the interaction between the upper rod 154a, lower rod 154c, and the arch wire 160 will cause the arch wire 160 to push against the upper rod 154a and the lower rod 154c, generating a clockwise torque on the bracket 122 (when viewed along a direction facing a right side of the bracket 122).

The first torque derived from the interaction of the arch wire 160 and the rods 154b, 154d can be different from the second torque derived from the interaction of the arch wire 160 and the rods 154a, 154c. For example, if the rods 154b, 154d push against the arch wire 160 with greater force, as compared to the rods 154a, 154c, then the first torque will be greater than the second torque. This provides the orthodontist greater flexibility in designing the proper force system applied to the tooth for alignment. For example, it is possible to set one gear (see FIG. 6) and corresponding rods to provide the required force, and use the opposing gear and corresponding rods to function as a stopper. Initially, the rods are set to provide some space for movement of the arch wire 160. The gear and corresponding rods provide the required force to move the arch wire 160 along a prescribed path resulting in correcting the alignment of the tooth. The opposing gear and corresponding rods stop the movement of the arch wire 160 at a prescribed end position.

In some examples, the vertical dimension (L1) of the bracket 122 is about 5 mm, the horizontal dimension (L2) of the bracket 122 is about 11 mm, and the thickness of the bracket 122 at its thickest portion is about 4 mm. The dimensions of the bracket 122 can vary depending on the size of the tooth being treated and the amount of force required. For example, the bracket for treating a molar tooth can be larger than a bracket for treating a canine tooth. A larger bracket may house a more powerful motor that can provide a greater force than that provided by a smaller bracket. The force exerted by the bracket 122 on the tooth can be, e.g., about 1 to 2 Newtons.

Figure 6:
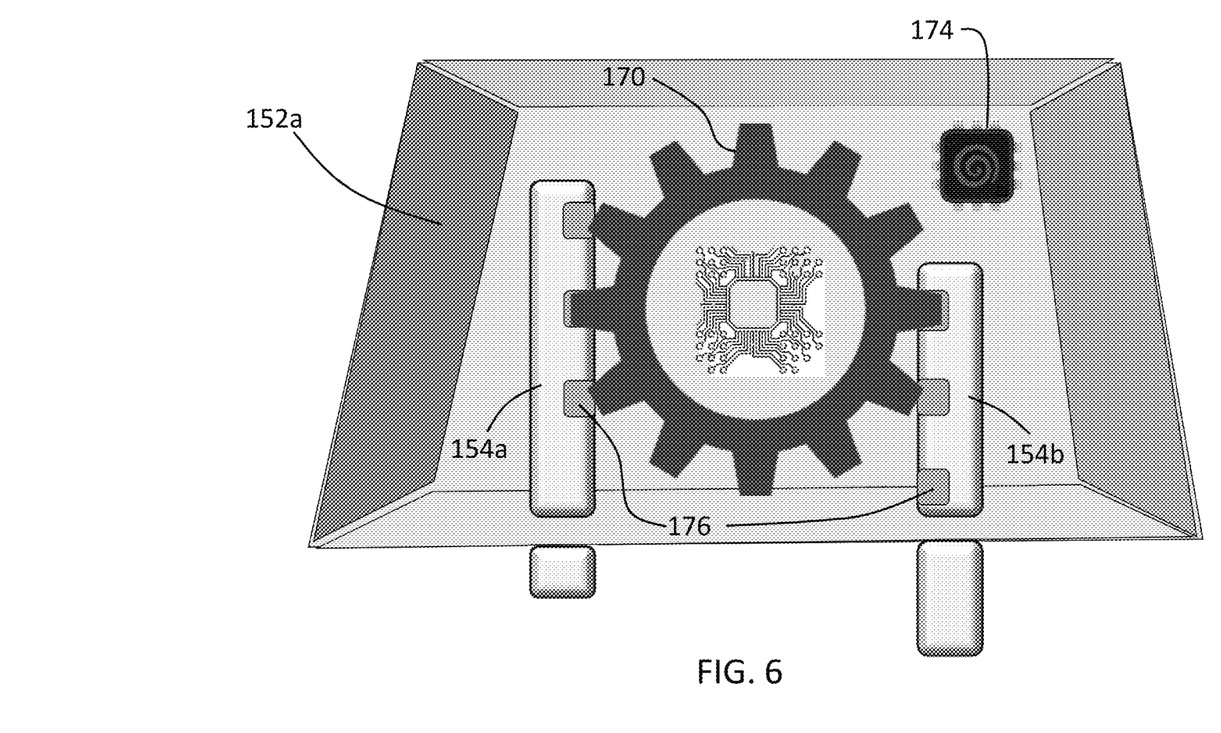
FIG. 6 is a diagram of an upper support module of the e-Right bracket.

Referring to FIG. 6, the upper support 152a supports a miniature gear 170 for driving the rods 154a, 154b up or down. The gear 170 is driven by a miniature motor (not shown in the figure). For example, the miniature gear 170 and miniature motor can be fabricated using micro electromechanical systems (MEMS) technology. The gear 170 engages notches 176 formed in the rods 154a, 154b. When the gear 170 rotates in a clockwise direction (when viewed from a direction facing the front side of the bracket 122), the gear 170 pushes the rod 154b downwards and pushes the rod 154a upwards. Conversely, when the gear 170 rotates in a counterclockwise direction, the gear 170 pushes the rod 154b upwards and pushes the rod 154a downwards.

An integrated circuit chip 174 includes circuitry for communicating with the computer server 104, the reader 108, and/or the mobile device 110. The chip 174 also includes circuitry for controlling the operation of the motor.

The upper support 152a provides a sealed environment for the motor, gear 170, and chip 174. The rods 154a, 154b protrude from the upper support 152a through small openings. The openings are made with precision and provided with insulating rubber linings to prevent liquids from entering the bracket. The gaps between the rods 154a, 154b and the edges of the openings are very small such that saliva or food particles do not enter through the gaps. The electrical contacts of the chip 174 and the motor can be sealed with, e.g., epoxy so that even if some fluid were to enter through the gaps, it would not affect the operation of the chip 174 and the motor.

The lower support 152b has a configuration similar to the upper support 152a. The lower support 152b also has a miniature motor and a miniature gear for driving the rods 154c, 154d. A chip controls the operations of the motor and gear. In some implementations, a single chip controls the operations of the motors in the upper support 152a and the lower support 152b. For example, the chip in the upper support 152a may send signals to the motor in the lower support 152b through signal lines that extend from the upper support 152a through the base 150 to the lower support 152b. The chip can also be placed in the base 150, in which the signal lines extend from the base to the upper and lower supports 152a, 152b.

The upper and lower gears can work in combination. For example, both the lower and upper gears can rotate in a clockwise direction, such that upper rod 154b exerts a downward force, the lower rod 154c exerts an upward force, resulting in a couple force system leading to a counter-clockwise rotation of the attached tooth around its center of rotation. In the example of FIG. 3, in which the tooth 140 in the lower right quadrant, the counter-clockwise rotation results in distal (backward) tipping that corrects the initial mesial (forward) tipping.

Figure 7:
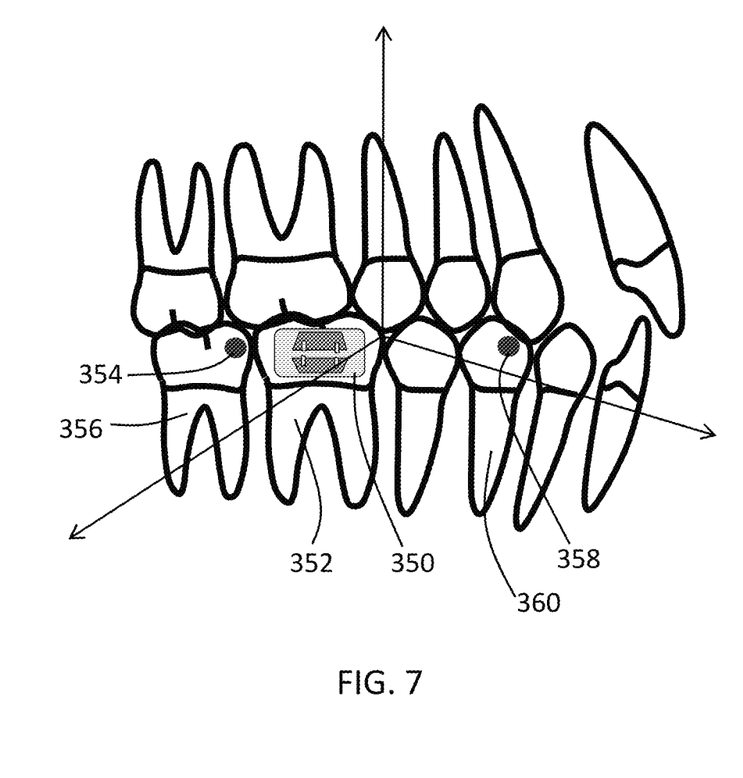
FIG. 7 is a diagram of a smart bracket and exemplary reference markers.

Various smart orthodontic brackets and wires have been described above. These smart brackets and wires can be used in the remote orthodontic system 100 of FIG. 1. Referring to FIG. 7, in order to monitor the movement of the tooth under treatment, markers can be attached to one or more adjacent teeth. For example, a smart bracket 350 is attached to a tooth 352 that needs to be aligned. A first marker 354 is attached to a tooth 356, and a second marker 358 is attached to another tooth 360. When the smart bracket 350 is first installed on the tooth 352, a set of one or more pictures of the teeth are taken. After a period of time, such as three or four weeks later, a second set of one or more pictures of the teeth are taken. The movement of the tooth 352 under treatment relative to the other teeth 356 and 360 can be measured by comparing the position of the bracket 350 relative to the markers 354 and 358 that function as reference points.

In some examples, the patient takes images of the teeth and sends them to the orthodontist, who monitors the progress of the treatment. If the movement of the tooth 352 is according to plan, then the smart bracket 350 will be adjusted according to plan. If the movement of the tooth 352 is outside of acceptable boundaries, then the orthodontist may adjust the treatment plan or ask the patient to return to the clinic for further examination and/or treatment. When the orthodontist needs to adjust the treatment plan, the orthodontist may send an instruction from the clinic terminal 106 to the server computer 104 to adjust the treatment plan stored locally at the server 104.

In some examples, the mobile phone 110 may execute an orthodontic app that provides instructions to the patient or a helper of the patient on how to take pictures in order to accurately determine the movement of the tooth 352. For example, a helper may use the camera on the mobile phone 110 to take pictures of the patient's teeth. A reference image that was previously taken can be overlaid on a live view taken by the phone camera. The reference image may show the two markers 354 and 358, so that the helper may position and orient the camera to take a picture of the teeth in which the markers 354 and 358 are at similar positions in the new picture. This makes it easier to compare the current picture with a previously taken picture to determine the movement of the tooth 352. A set of orthodontic biomechanical algorithms can be used by the system 100 to determine the auto adjustments to be made to the smart brackets, such as increasing or decreasing the forces applied by the gears in the e-Right brackets.

The smart brackets may have sensors for sensing the force applied to the corresponding tooth. For example, a microelectromechanical sensor system having piezoresistive microsensors attached between the smart bracket and the tooth can be used to take measurements that can be used to calculate forces applied to the tooth in the x, y, and z directions, and moments in the x, y, and z directions. By monitoring the forces actually applied to the tooth, the system 100 can determine whether the gears in the smart brackets need to be adjusted to apply more or less force in a certain direction.

The chip 174 (FIG. 6), the miniature motors, and the sensors system can be powered wirelessly by beaming power to microcoils in the smart brackets. The chip 174 may include circuitry for modulating data sent to the reader 108 or the server 104, or demodulating the signals sent from the reader 108 or the server 104.

The remote orthodontic system 100 helps orthodontists and their patients to have a high quality orthodontic treatment, with reduced visits to the dental office and reduced costs. For example, the adjustments to the smart brackets and arch wires can be made while the patients are at home. The orthodontists can also monitor the treatments and make adjustments to the treatment plans from home, allowing more flexible work schedules.

A novel orthodontic bracket that can generate and deliver forces has been described above. The system 100 is interactive in which the patient and the treatment provider are able to monitor the status of teeth alignment and report responses and symptoms. The system can be remotely controlled, enabling quick re-adjustment and auto-correction. The system can apply biomechanical equations based on the known static and dynamic equilibrium laws and algorithms. The system provides treatments with predictable and improved outcomes, so the treatment duration can be accurately forecasted and better controlled.

Each of the computer server 104, mobile phone 110, and reader 108 can include one or more processors and one or more computer-readable mediums (e.g., RAM, ROM, SDRAM, hard disk, optical disk, and flash memory). The one or more processors can perform various calculations or control functions described above. The calculations and various functions can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., DRAM) and transmission media. Transmission media includes, without limitation, coaxial cables, copper wire and fiber optics.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory (ROM) or a random access memory (RAM) or both. The essential elements of a computer are a processor for executing instructions and one or more memories for storing instructions and data. Generally, a computer will also include, or be operatively coupled to communicate with, one or more mass storage devices for storing data files. The mass storage devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM, CD-R, DVD-ROM, DVD-R, Blu-ray DVD disks. The processor and the memory can be supplemented by, or incorporated in, ASICs (application-specific integrated circuits). The chip 174 (FIG. 6) may include one or more processors described above. The chip 174 may also include one or more volatile or non-volatile memories for storing instructions to be executed by the one or more processors.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Other embodiments are within the scope of the following claims. For example, a combination of various types of smart brackets can be used for treating one patient. The smart brackets and arch wires can be made of materials different from those described above.

What is claimed is:

1. An orthodontic bracket, comprising:
   a base configured to be attached to a surface of a tooth;
   a first member and a second member both attached to the base, the first and second members being spaced apart to define an archwire slot configured to receive an archwire,
   wherein the first member comprises a first gear and a first rod, the first rod has a first portion having notches that engage the gear, the first rod has a second portion that extends into the archwire slot, when the first gear rotates in a specified direction, the first gear drives the first rod in which the first rod is configured to contact the archwire and apply a first force to the archwire.

2. The orthodontic bracket of claim 1 in which the second member comprises a second gear and a second rod, the second rod has a first portion having notches that engage the second gear, the second rod has a second portion that extends into the archwire slot, when the second gear rotates in a specified direction, the second gear drives the second rod in which the second rod is configured to contact the archwire and apply a second force to the archwire.

3. The orthodontic bracket of claim 2 in which the first member comprises a third rod, the third rod has a first portion having notches that engage the first gear, the third rod has a second portion that extends into the archwire slot,
   the first and third rods engage opposing sides of the first gear such that when the first gear rotates, the first and third rods move in opposite directions in which one of the first and third rods extends further into the archwire slot while the other of the first and third rods extends less into the archwire slot.

4. The orthodontic bracket of claim 3 in which the second member comprises a fourth rod, the fourth rod has a first portion having notches that engage the second gear, the fourth rod has a second portion that extends into the archwire slot, the second and fourth rods engage opposing sides of the second gear such that when the second gear rotates, the second and fourth rods move in opposite directions in which one of the second and fourth rods extends further into the archwire slot while the other of the second and fourth rods extends less into the archwire slot.

5. The orthodontic bracket of claim 4 in which the first rod is positioned at a first distance from the base, the second rod is positioned at a second distance from the base, the third rod is positioned at a third distance from the base, the fourth rod is positioned at a fourth distance from the base, the first distance is different from the second distance, and the third distance is different from the fourth distance.

6. The orthodontic bracket of claim 5 in which the first distance is the same as the third distance, and the second distance is the same as the fourth distance.

7. The orthodontic bracket of claim 2 in which the second member comprises a third rod, the third rod has a first portion having notches that engage the second gear, the third rod has a second portion that extends into the archwire slot, the second and third rods engage opposing sides of the second gear such that when the second gear rotates, the second and third rods move in opposite directions in which one of the second and third rods extends further into the archwire slot while the other of the second and third rods extends less into the archwire slot.

8. The orthodontic bracket of claim 1, further comprising a cover attached to the first and second members, in which the cover is configured to retain the archwire within the archwire slot.

9. The orthodontic bracket of claim 2 in which the first gear is configured to be driven manually.

10. The orthodontic bracket of claim 9 in which the second gear is configured to be driven manually.

11. The orthodontic bracket of claim 2 in which the first rod is positioned at a first distance from the base, the second rod is positioned at a second distance from the base, and the first distance is different from the second distance.

12. The orthodontic bracket of claim 1, comprising a first miniature motor to drive the first gear.

13. The orthodontic bracket of claim 12, comprising a wireless energy transfer module to receive energy wirelessly for powering the first motor.

14. The orthodontic bracket of claim 12, comprising an integrated circuit having circuitry to control the first motor.

15. The orthodontic bracket of claim 14 in which the integrated circuit comprises a communication module to communicate wirelessly with an external device.

16. The orthodontic bracket of claim 15 in which the integrated circuit is configured to receive instructions wirelessly and to control the first motor according to the instructions.

17. The orthodontic bracket of claim 1, comprising a sensor to detect a force applied by the bracket to the tooth.

18. The orthodontic bracket of claim 17, comprising a wireless energy transfer module to receive energy wirelessly for powering the sensor.

19. The orthodontic bracket of claim 1, comprising a radio frequency identification tag associated with a unique identifier.

20. A method comprising:
attaching a base of an orthodontic bracket to a surface of a tooth, the orthodontic bracket having a base, a first member and a second member, the first member and the second member being attached to the base and spaced apart to define an archwire slot,
the first member comprising a first gear and a first rod, the first rod having a first portion having notches that engage the first gear, the first rod having a second portion that extends into the archwire slot,
inserting an archwire into the archwire slot; and
rotating the first gear to drive the first rod to contact the archwire and apply a first force to the archwire.

21. The method of claim 20 in which the second member comprises a second gear and rod, the second rod having a first portion having notches that engage the second gear, the second rod having a second portion that extends into the archwire slot, and
the method comprises rotating the second gear to drive the second rod to contact the archwire and apply a second force to the archwire.

22. The method of claim 21 in which the first member comprises a third rod, the third rod has a first portion having notches that engage the first gear, the third rod has a second portion that extends into the archwire slot, the first and third rods engage opposing sides of the first gear, and
the method comprises rotating the first gear to drive the first and third rods to move in opposite directions in which one of the first and third rods extends further into the archwire slot while the other of the first and third rods extends less into the archwire slot.

23. The method of claim 22, comprising rotating the first gear, driving the first and third rods to apply and guide different forces to the archwire, causing the archwire to support a rotational force that is applied to the bracket and transmitted to the tooth, the rotational axis being along a lingual-facial direction.

24. The method of claim 22 in which the second member comprises a fourth rod, the fourth rod has a first portion having notches that engage the second gear, the fourth rod has a second portion that extends into the archwire slot, the second and fourth rods engage opposing sides of the second gear; and
the method comprises rotating the second gear to drive the second and fourth rods to move in opposite directions in which one of the second and fourth rods extends further into the archwire slot while the other of the second and fourth rods extends less into the archwire slot.

25. The method of claim 24, comprising rotating the first and second gears, driving the first and third rods to apply different forces to the archwire, driving the second and fourth rods to apply different forces to the archwire, causing the archwire to provide a rotational force that is applied to the bracket and transmitted to the tooth, the rotational axis being along a lingual-facial direction.

26. The method of claim 24 in which the first rod is positioned at a first distance from the base, the second rod is positioned at a second distance from the base, the third rod is positioned at a third distance from the base, the fourth rod is positioned at a fourth distance from the base, the first distance is different from the second distance, and the third distance is different from the fourth distance.

27. The method of claim 26, comprising rotating the first and second gears to drive the first and third rods to apply forces to first locations of a first surface of the archwire, and to drive the second and fourth rods to apply forces to second locations of a second surface of the archwire, the first locations being at a distance from the base that is different from the distance of the second locations from the base, causing the archwire to provide a rotational force that is applied to the bracket and transmitted to the tooth.

28. The method of claim 26 in which the first distance is the same as the third distance, and the second distance is the same as the fourth distance.

29. The method of claim 21 in which the second member comprises a third rod, the third rod has a first portion having notches that engage the second gear, the third rod has a second portion that extends into the archwire slot, the second and third rods engage opposing sides of the second gear;

the method comprising rotating the second gear to drive the second and third rods in opposite directions in which one of the second and third rods extends further into the archwire slot while the other of the second and third rods extends less into the archwire slot.

30. The method of claim 21, further comprising attaching a cover to the first and second members to retain the archwire within the archwire slot.

31. The method of claim 21, comprising manually rotating the first gear to drive the first rod.

32. The method of claim 31, comprising manually rotating the second gear to drive the second rod.

33. The method of claim 20 in which the first rod is positioned at a first distance from the base, the second rod is positioned at a second distance from the base, and the first distance is different from the second distance.

34. The method of claim 20, comprising driving a first motor to rotate the first gear.

35. The method of claim 34, comprising providing energy wirelessly to a wireless energy transfer module to power the first motor.

36. The method of claim 34, comprising operating an integrated circuit to control the first motor.

37. The method of claim 36, comprising operating the integrated circuit to communicate wirelessly with an external device.

38. The method of claim 37, comprising at the integrated circuit, receiving instructions wirelessly from the external device and controlling the first motor according to the instructions.

39. The method of claim 20, comprising using a sensor to sense a force applied by the bracket to the tooth.

40. The method of claim 39, comprising providing energy wirelessly to a wireless energy transfer module to power the sensor.

41. The method of claim 20, comprising probing a radio frequency identification tag attached to the bracket to identify a unique identifier associated with the tag.

42. An orthodontic bracket, comprising:
a base configured to be attached to a surface of a tooth;
an occlusal member and a gingival member both attached to the base, the occlusal member and the gingival member being spaced apart to define an archwire slot between a gingival surface of the occlusal member and an occlusal surface of the gingival member, the archwire slot configured to receive an archwire,
wherein the occlusal member comprises a first miniature gear and a first miniature rod that function as a rack and pinion gear system, the first rod has an occlusal portion having notches that engage the gear, the first rod has a gingival portion that protrudes through the gingival surface of the occlusal member into the archwire slot, when the first gear rotates in a specified direction, the first gear drives the first rod in which the first rod is configured to contact the archwire and apply a first force to the archwire.

43. The orthodontic bracket of claim 42 in which the gingival member comprises a second miniature gear and rod that function as a rack and pinion gear system, the second rod has a gingival portion having notches that engage the second gear, the second rod has an occlusal portion that protrudes through the occlusal surface of the gingival member into the archwire slot, when the second gear rotates in a specified direction, the second gear drives the second rod in which the second rod is configured to contact the archwire and apply a second force to the archwire.

* * * * *